United States Patent
Lodwig et al.

(10) Patent No.: US 10,743,798 B2
(45) Date of Patent: Aug. 18, 2020

(54) METHOD AND APPARATUS FOR AUTOMATED DETECTION OF SUPPRESSION OF TEOAE BY CONTRALATERAL ACOUSTIC STIMULATION

(71) Applicants: Andre Lodwig, Worthsee (DE); Johann Oswald, Grafing (DE); Thomas Janssen, Tuntenhausen (DE)

(72) Inventors: Andre Lodwig, Worthsee (DE); Johann Oswald, Grafing (DE); Thomas Janssen, Tuntenhausen (DE)

(73) Assignee: PATH medical GmbH (DE)

( * ) Notice: Subject to any disclaimer, the term of this patent is extended or adjusted under 35 U.S.C. 154(b) by 459 days.

(21) Appl. No.: 15/134,657

(22) Filed: Apr. 21, 2016

(65) Prior Publication Data

US 2016/0256083 A1 Sep. 8, 2016

Related U.S. Application Data

(63) Continuation-in-part of application No. 14/294,283, filed on Jun. 3, 2014, now abandoned.

(51) Int. Cl.
*A61B 5/12* (2006.01)
*A61B 5/00* (2006.01)
A61B 5/0484 (2006.01)

(52) U.S. Cl.
CPC ............ *A61B 5/125* (2013.01); *A61B 5/7217* (2013.01); *A61B 5/04845* (2013.01); *A61B 5/4047* (2013.01); *A61B 5/4052* (2013.01); *A61B 5/7235* (2013.01)

(58) Field of Classification Search
None
See application file for complete search history.

(56) References Cited

U.S. PATENT DOCUMENTS

| | | | |
|---|---|---|---|
| 3,808,354 A | 4/1974 | Feezor et al. | |
| 5,655,540 A | 7/1997 | Seegobin | |
| 5,697,379 A | 12/1997 | Neely et al. | |
| 5,811,681 A | 9/1998 | Braun | |
| 6,110,126 A | 8/2000 | Zoth | |
| 6,186,958 B1 | 2/2001 | Katzman et al. | |
| 6,331,164 B1 | 12/2001 | Shaw et al. | |
| 2003/0216660 A1* | 11/2003 | Ben-Oren | A61B 5/083 600/532 |

(Continued)

OTHER PUBLICATIONS

Hamburger, A. et al., "Contralateral Acoustic Effect of Transient Evoked Otoacoustic Emissions in Neonates", International Tinnitus Journal, vol. 4, (1998) p. 35-57.

(Continued)

*Primary Examiner* — Matthew Kremer
(74) *Attorney, Agent, or Firm* — Marcus G. Theodore

(57) ABSTRACT

The invention is directed to a method of generating and measuring transiently evoked otoacoustic emissions (TEOAE) acoustic signals generated in the cochlea using a scheme of stimulating both inner ears simultaneously, left ear alone, and right ears alone with at least two different first and second averaging buffers per ear in a switching scheme with automated detection of contralateral suppression of TEOAE via statistical analysis of the differences of suppressed and unsuppressed responses.

17 Claims, 9 Drawing Sheets

(56) References Cited

U.S. PATENT DOCUMENTS

| | | | | |
|---|---|---|---|---|
| 2008/0221401 A1* | 9/2008 | Derchak | ............ | A61B 5/16 |
| | | | | 600/301 |
| 2009/0124874 A1* | 5/2009 | Gono | ............ | A61B 5/14539 |
| | | | | 600/341 |
| 2010/0030096 A1* | 2/2010 | Bradley | ............ | A61B 5/04845 |
| | | | | 600/544 |
| 2010/0204586 A1* | 8/2010 | Pu | ............ | A61B 5/4818 |
| | | | | 600/484 |
| 2010/0324437 A1* | 12/2010 | Freeman | ............ | A61B 5/085 |
| | | | | 600/529 |
| 2011/0022352 A1* | 1/2011 | Fujita | ............ | A61B 5/1036 |
| | | | | 702/160 |
| 2012/0101372 A1* | 4/2012 | Teramura | ............ | A61B 5/0066 |
| | | | | 600/425 |
| 2013/0018239 A1* | 1/2013 | Lisogurski | ............ | A61B 5/0004 |
| | | | | 600/322 |
| 2013/0303940 A1* | 11/2013 | Saly | ............ | A61B 5/123 |
| | | | | 600/559 |
| 2013/0317319 A1* | 11/2013 | Huang | ............ | A61B 5/7271 |
| | | | | 600/301 |

OTHER PUBLICATIONS

Dirante, A. Spada, "Contralateral Supression of Lin. and Nonlinear Transient Evoked Otoa-coustic Emissions in Neonates at Risk for Hearing Loss", J.ofComm.Dis,41-2008—p. 70-73.

* cited by examiner

Fig. 1
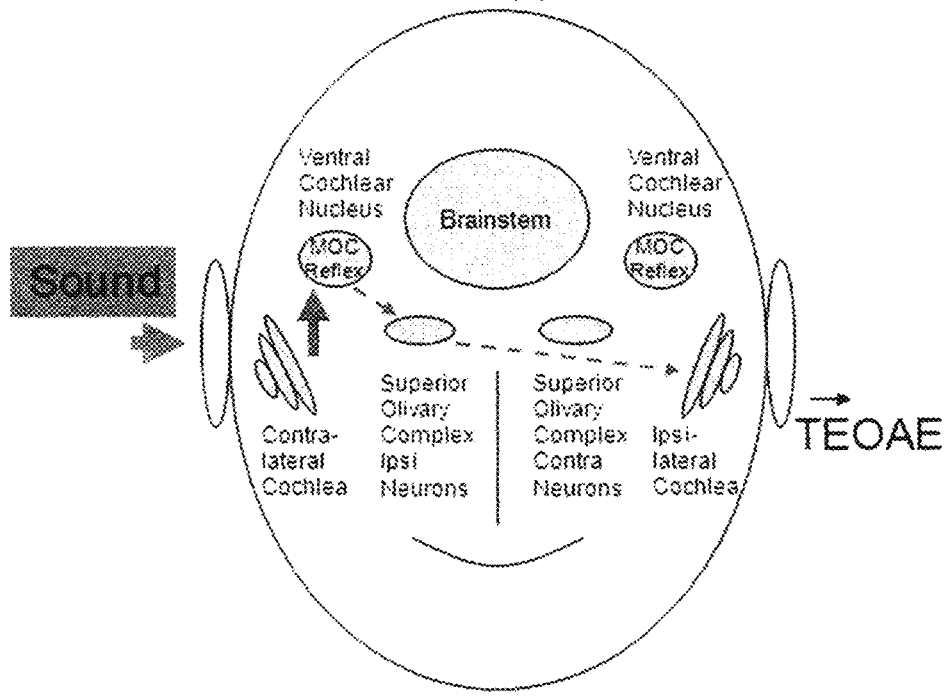
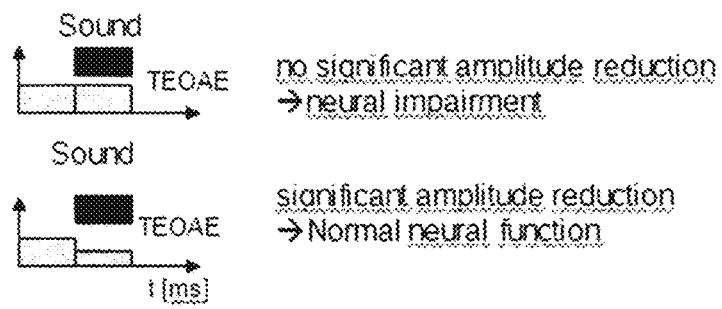
PRIOR ART

Fig. 4

| No. of frames | Stim L | Stim R | Rec L A | Rec L B | Rec R A | Rec R B |
|---|---|---|---|---|---|---|
| 10 | X | | X | | | |
| 2 | X | X | | | | |
| 5 | X | X | | X | | X |
| 2 | | X | | | | |
| 10 | | X | | | X | |
| 2 | X | X | | | | |
| 5 | X | X | | X | | X |
| 2 | X | | | | | |
| SUM | | | 10 | 10 | 10 | 10 |

Stim L: Stimulate left ear

Stim R: Stimulate right ear

Rec L A: record left ear into left A buffer

Rec L B: record left ear into left B buffer

Rec R A: record left ear into right A buffer

Rec R B: record left ear into right B buffer

This sequence would record each ear's unsuppressed TEOAE into its 'A' buffer, and each ear's suppressed TEOAE into its 'B' Buffer. A complete cycle takes 38 frames and results in 10 frames averaged into each of the 4 buffers.

METHOD AND APPARATUS FOR AUTOMATED DETECTION OF SUPPRESSION OF TEOAE BY CONTRALATERAL ACOUSTIC STIMULATION

CROSS-REFERENCED RELATED APPLICATIONS

This patent application is a continuation-in-part patent application of the U.S. patent application entitled "Method and apparatus for Automated Detection of Suppression of TEOAE by Contralateral Acoustic Stimulation", Ser. No. 14/294,283, filed Jun. 3, 2014.

STATEMENT REGARDING FEDERALLY SPONSORED RESEARCH OR DEVELOPMENT

NONE

REFERENCE TO A SEQUENCE LISTING

NONE

BACKGROUND OF THE INVENTION

Field:

The invention relates to the measurement of transiently evoked otoacoustic emissions (TEOAE), acoustic signals generated in the cochlea. In particular, it relates to the automated detection of contralateral suppression of TEOAE.

State of the Art:

Otoacoustic emissions (OAEs) are sounds actively generated in the inner ear. There are two types of otoacoustic emissions: spontaneous otoacoustic emissions (SOAEs), which can occur without external stimulation, and evoked otoacoustic emissions (EOAEs), which require an evoking stimulus. OAE can be measured with a small probe inserted into the ear canal.

People with normal hearing produce emissions. Those with hearing loss produce less or no OAE. Ears with cochlear hearing losses of more than 50 dB will normally not produce OAE.

EOAEs are currently evoked using three different methodologies: Stimulus Frequency OAEs (SFOAEs), Transient-evoked OAEs (TEOAE), and Distortion product OAEs (DPOAEs). SFOAEs are measured during the application of a pure-tone stimulus, and are detected by the vectorial difference between the stimulus waveform and the recorded waveform (which consists of the sum of the stimulus and the OAE). TEOAE are evoked using a click (broad frequency range) or toneburst (brief duration pure tone) stimulus. The evoked response from a click covers a frequency range that depends on the frequency range of the stimulus, typically up to around 4 kHz. A toneburst will elicit a response from the cochlear region that has the same frequency as the pure tone. DPOAEs are evoked using a pair of primary tones $f_1$ and $f_2$ with particular sound pressure level (usually either 65-55 dBSPL or 65 for both) and ratio ($f_1:f_2$). The evoked responses from these stimuli occur at frequencies ($f_{dp}$) mathematically related to the primary frequencies, with the two most prominent being $f_{dp}=2f_1-f_2$ (the "cubic" distortion tone, most commonly used for hearing screening) and $f_{dp}=f_2-f_1$ (the "quadratic" distortion tone, or simple difference tone).

OAE are usually recorded with an averaging scheme, which takes advantage of the fact that the OAE signal is phase locked to the stimulus, while external noise is not. This results in the OAE signal being added in the averaging process, while noise is reduced.

For TEOAE, a so-called nonlinear stimulus sequence is often used to reduce stimulus artifacts in the recording. This makes use of the fact that TEOAE amplitude is not proportional to the stimulus amplitude. The stimulus is typically constructed from 4 single clicks, one of which is 3 times bigger in amplitude than the others. If the responses to the 3 lower amplitude clicks are subtracted from the response to the high-amplitude click, all linear components of the response, including stimulus artifacts, are cancelled out. One presentation and recording of such a sequence will hereafter be referred to as a frame.

There is an effect called contralateral suppression in OAF, which means that the OAE that can be recorded at one ear ("ipsilateral") is influenced by acoustic stimulation of the other ear (contralateral). The contralateral acoustic stimulation is usually referred to as "CAS".

OAE CAS suppression is thought to be caused by the efferent auditory system. The general concept of TEOAE CAS suppression is shown in FIG. 1.

This suppression effect will normally reduce the OAF level in the order of less than 1 dB, and can be seen in both TEOAE and DPOAE In the case of DPOAE, CAS can produce suppression and also enhancement, depending on the presence of DPOAE fine structure at the frequency under test. DPOAE CAS suppression effects can be as high as 10 dB for single frequencies. However, since fine structure differs strongly between subjects, suitable frequencies have to be determined in a pre-measurement before the actual DPOAE suppression test is actually done. This makes the procedure inconvenient for a fast, automated test.

OAE are generated by the so-called outer hair cells in the cochlea, which act as an amplifier for soft sounds. Outer hair cells are connected to efferent nerve fibers, which can influence their motility and thus the generation of OAE.

The presence of OAE CAS suppression therefore does not only indicate cochlea functionality, but also the function of the efferent system on the ipsilateral ear and the afferent system on the contralateral ear The auditory brainstem response (ABR) test gives information about the inner ear (cochlea) and brain pathways for hearing. This test is more generally referred to as auditory evoked potential (AEP). The ABR is also indicated for a person with signs, symptoms, or complaints suggesting a type of hearing loss on the auditory pathway.

The ABR is performed by pasting electrodes onto the head—similar to electrodes placed around the heart when an electrocardiogram is run—and recording electrical activity in response to sound. The person being tested preferably rests quietly or sleeps while the test is performed.

One normally needs to record ABR to check for retrocochlear disorders, which includes placing electrodes on the scalp and using electro-acoustic transducers for acoustic stimulation. In contrast, OAE CAS recording only needs the placement of two OAE probes.

CAS suppression in TEOAE in general is known, but not widely used mainly because the level difference between suppressed and unsuppressed recording of TEOAE is less than 1 dB and is hard to detect reliably; especially if noise, changes in sound probe placement or static pressure in the middle ear are present during testing.

To reduce artificial differences between the suppressed and unsuppressed measurement, tests are usually repeated, such as suppressed—unsuppressed—suppressed—unsuppressed. A constant drift of probe placement could then be separated from the suppression effect.

The difficulty in detecting this small level difference requires long test times, because detection of small level differences requires a high level accuracy, and is correlated to averaging time. Repetitions as described above further extend overall test time.

There thus remains a need for a fast, reliable, automated OAE CAS suppression test. The method and apparatus described below provides such a test.

BRIEF SUMMARY OF THE INVENTION

The method and apparatus to automatically detect TEOAE contralateral suppression comprises:

a. stimulating Transiently-evoked Otoacoustic emissions (TEOAEs) given off by the inner ear using a click (broad frequency range) or tone burst (brief duration pure tone) or similar stimulus. Particularly, a non-linear stimulus sequence can be used to reduce stimulus artifacts.

b. recording TEOAE with and without suppression in a cycling/alternating scheme in at least two separate averaging buffers per ear, using a signal as the suppressor that also evokes TEOAE in the contralateral ear.

c. applying signal statistical methods to the averaged recordings of suppressed and unsuppressed case to automatically detect suppression, other than just comparing the overall level of the suppressed and unsupressed TEOAE. A preferred statistical method is to calculate the difference trace of suppressed and unsuppressed TEOAE and estimate the statistical significance of this signal by comparing it to a statistical noise estimator.

In invented method, the TEOAE stimulus is used as the contralateral suppressor signal for the other ear. This method employs a stimulus sequence that records TEOAE suppressed and unsuppressed on both ears by periodically switching between stimulating both ears, left ear alone and right ear alone. Thus, a result for both ears is acquired in one test run. Stimulation-only frames with no recording can be inserted to allow settling of the suppression effect. No-stimulus-frames can be inserted to allow recovery from suppression.

Settling and recovery of the CAS suppression effect takes in the order of 200 ms, therefore the extra frames with no recording provide better separation of the suppressed and unsuppressed results.

A possible periodic sequence is shown in FIG. 2. First, the left ear is stimulated, and the TEOAE recorded in the left ear's A buffer. Then, 2 frames of binaural stimulation are inserted with no recording (settling phase). Then, both ears are stimulated, and each ear's TEOAE recorded in that ear's B buffer. After two recovery frames, the right ear only is stimulated, and the resulting TEOAE signal is recorded in the right ear's A buffer. After two more settling frames it switches back to stimulating both ears and so forth. After one cycle of this example sequence, each buffer received 10 averaged frames. The sequence would typically need to be repeated 10 to 100 times, resulting in 100 to 1000 averages.

The protocol is set up to achieve an equal number of averages in each buffer after one cycle, and to be symmetrical in switching left and right ear. This is convenient for statistical analysis but not mandatory. All buffers typically represent a time domain signal of 10 to 15 ms, sampled with a standard audio sampling rage of, for example, 16 kHz.

The method uses at least two averaging buffers per ear, allowing collecting suppressed and unsuppressed TEOAE separately as described above. In the sequence as described above, the A buffer of each ear would contain the unsuppressed TEOAE waveform, and the B buffer would contain the suppressed TEOAE waveform.

Additional buffers may be introduced, for example to record TEOAE in the settling/recovery phase after switching the suppressor on or off. This additional information could, for example, be used to acquire information about the CAS suppression delay or decay.

A standard way of measuring the suppression effect would be to compare the sound level of suppressed TEOAE (as recorded in the B buffer) to the sound level of the unsuppressed TEOAE (as recorded in the A buffer). This value alone does not give reliable information if TEOAE CAS suppression is actually present or not, since noise and other effects may also create such level differences.

The invention described herein involves applying signal statistical methods to verify suppression.

A preferred variation of the method employs signal statistical detection comprised of subtracting the suppressed averaging buffer recording from the unsuppressed averaging buffer recording for each ear and then performing a statistical evaluation of the resulting difference trace.

In one preferred variation, the statistical evaluation of the difference trace involves counting significant peaks which exceed a given amplitude above the estimated standard deviation "sigma" (typically 3 sigma). The standard deviation can be calculated from the overall signal energy that has been averaged in each of the buffers.

In another application, the statistical evaluation involves comparing the root mean square (RMS) amplitude of the difference trace to its estimated standard deviation Alternative statistical methods, such as spectral comparison, Fsp values, cross-correlations, can also be used within the scope of this invention.

The suppression results may be illustrated in a number of formats. For example, the final result for one or both ears if TEOAE suppression has been detected may be displayed as a numeric output, or may be displayed in a screening manner ("PASS vs REFER").

Usually, the base method testing stops automatically when TEOAE suppression is detected on one or both ears. The recording sequence, stimulus levels, stop criteria and other parameters are user configurable and/or selectable, In one variation, the recording sequence can automatically change as soon as suppression has been detected on one ear, in such a way that it skips that ear's single stimulation slots to speed up the remaining testing progress for the other ear.

The testing method may also add an extra sinusoidal tone to the stimulus for feedback of this tone to monitor probe stability. This tone would have a low frequency of typically 440 Hz and a moderate sound level of typically 30 dB SPL.

Heretofore, an automated procedure was not available with a clear outcome "suppression detected" or "suppression not detected".

The basic components of the apparatus for performance the automated OAE CAS suppression tests comprise:

a) a digital sound processing hardware, providing stimulus generation and recording of microphone signals from OAE probes b) two OAE probes, each containing at least one microphone and one loudspeaker c) a software that implements the method as described above, either running on the apparatus itself or on a separate interconnected computational device, and d) means for powering and operating the apparatus and displaying the test results.

Optional recorders and transmitters may be included to interconnect and transmit signals to a remote center for online monitoring.

The foregoing method and apparatus thus provides a fast, reliable, automated OAE CAS suppression test.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1 illustrates the general concept of TEOAE CAS suppression.

FIG. 4 illustrates a Table of a periodic sample sequence to record TEOAE CAS suppression of the method of FIG. 3.

DETAILED DESCRIPTION OF THE INVENTION

Figure 2:
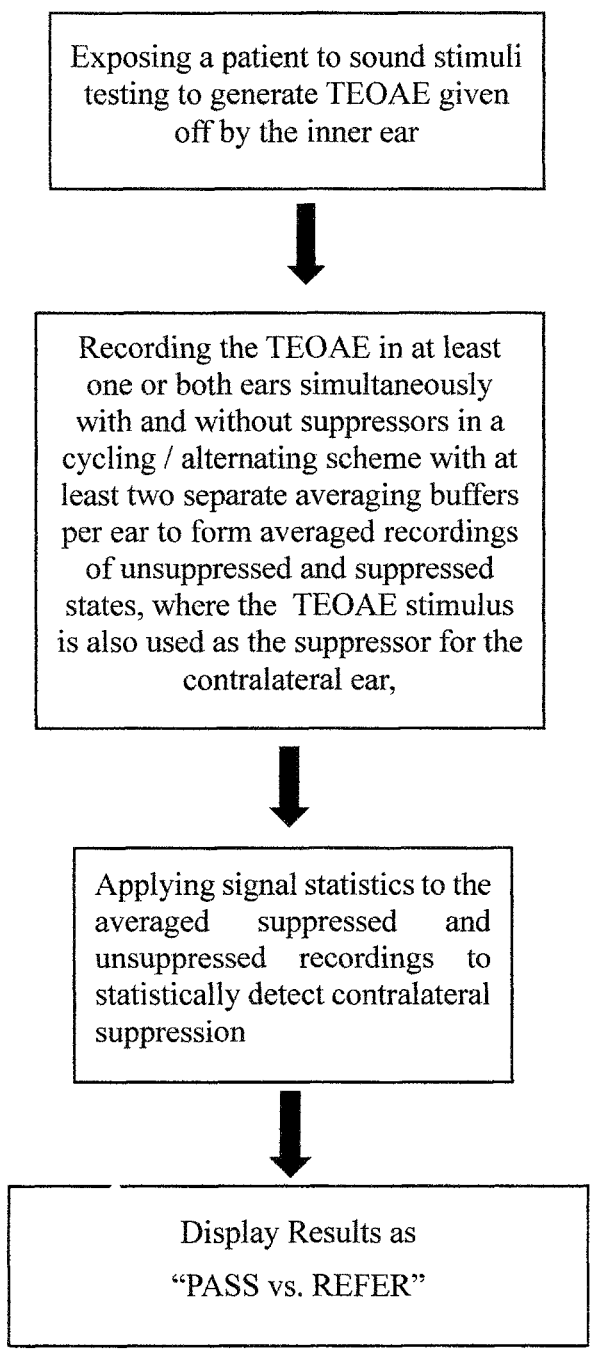
FIG. 2 illustrates the general method of the TEOAE recording and suppression method.

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the method of the present invention, as represented in FIGS. 1 through 5, is not intended to limit the scope of the invention, as claimed, but is merely representative of presently preferred embodiments of the invention.

An otoacoustic emission (OAE) is a sound which is generated from within the inner ear. Otoacoustic emissions have since been shown to arise through a number of different cellular and mechanical causes within the inner ear. OAEs disappear after the inner ear has been damaged, so OAEs are often used as a measure of inner ear health.

Broadly speaking, there are two types of otoacoustic emissions: spontaneous otoacoustic emissions (SOAEs), which can occur without external stimulation, and evoked otoacoustic emissions (EOAEs), which require an evoking stimulus.

Transient-evoked OAEs (TEOAEs) are evoked using a click (broad frequency range) or tone burst (brief duration pure tone) stimulus. The evoked response from a click covers the frequency range up to around 4 kHz, while a tone burst will elicit a response from the region that has the same frequency as the pure tone.

Contralateral suppression in OAE is influenced by acoustic stimulation of the other ear (contralateral). The contralateral acoustic stimulation is usually referred to as "CAS". OAE CAS suppression is thought to be caused by the efferent auditory system. The general concept of TEOAE CAS suppression is shown in FIG. 1. As illustrated, suppressor sound enters the ear denoted "contralateral". This sound is then processed via the Ventral Cochlear Nucleus, and Superiour Olivary Complex to finally influence the ipsilateral cochlea.

TEOAE are evoked and recorded on the ear denoted as "ipsilateral". The TEOAE generation is influenced by the contralateral acoustic stimulation (CAS) as described above.

The olivocochlear bundle (OCB) originates in the superior olivary complex in the brainstem. The vestibulocochlear anastomosis carries the efferent axons into the cochlea, where they innervate the organ of Corti (OC). The OCB contains fibres projecting to both the ipsilateral and contralateral cochleae, prompting an initial division into crossed (COCB) and uncrossed (UCOCB) systems. More recently, however, the division of the OCB is based on the cell bodies' site of origin in the brainstem relative to the medial superior olive (MSO). The medioventral periolivary (MVPO) region, also known as the ventral nucleus of the trapezoid body, comprises a diffuse region of neurons located medial to the MSO, and gives rise to the medial olivocochlear system (MOCS). Acoustic stimulation of the inner hair cells send a neural signal to the posteroventral cochlear nucleus (PVCN), and the axons of the neurons from the PVCN cross the brainstem to innervate the contralateral MOC neurons. In most mammals, the MOC neurons predominantly project to the contralateral side (forming the ipsilateral reflex), with the remainder projecting to the ipsilateral side (forming the contralateral reflex).

The strength of the reflex is weakest for pure tones, and becomes stronger as the bandwidth of the sound is increased; hence the maximum MOCS response is observed for broadband noise. Some studies have measured the effects of stimulating the MOCS with sound that showed the contralateral sound (resulting in MOCS stimulation) reduced the N1 potential—a suppression which was eliminated upon transection of the olivocochlear bundle (OCB). In humans, the largest amount of evidence for the action of efferents has come from the suppression of otoacoustic emissions (OAEs) following acoustic stimulation.

CAS TEOAE provide information on the functionality of (i) afferent nerve fibers between cochlea and medial olivocochlear system (MOC) of the contralateral ear and (ii) efferent nerve fibers between (MOC) and cochlea of the ipsilateral ear.

Moreover, (i) onset time (about 200 ms)—time between stimulus onset and steady state of OAE amplitude—and (ii) offset time (about 200 ms)—time between stimulus offset and ground line—may give additional information on the functionality of the afferent and efferent hearing system.

Since typical TEOAE stimuli are wide-band, they can also be used as a contralateral suppressor. Doing so is one preferred variant of the invention.

If there is no significant amplitude reduction, this implies neural impairment. If there is significant amplitude reduction, this implies normal neural function.

FIG. 2 illustrates a flow chart of the general TEOAE recording and suppression sequence of the present method. The method to automatically detect Transient-evoked Otoacoustic emissions (TEOAE) contralateral suppression comprises:

a. exposing a patient to sound stimuli testing to generate TEOAE given off by the inner ear, b. recording the TEOAE in at least one or both ears simultaneously with and without suppressors in a cycling/alternating scheme with at least two separate averaging buffers per ear to form averaged recordings of unsuppressed and suppressed states, where the TEOAE stimulus is also used as the suppressor for the contralateral ear, and c. applying signal statistics to the averaged suppressed and unsuppressed recordings to statistically detect contralateral suppression.

Figure 3:
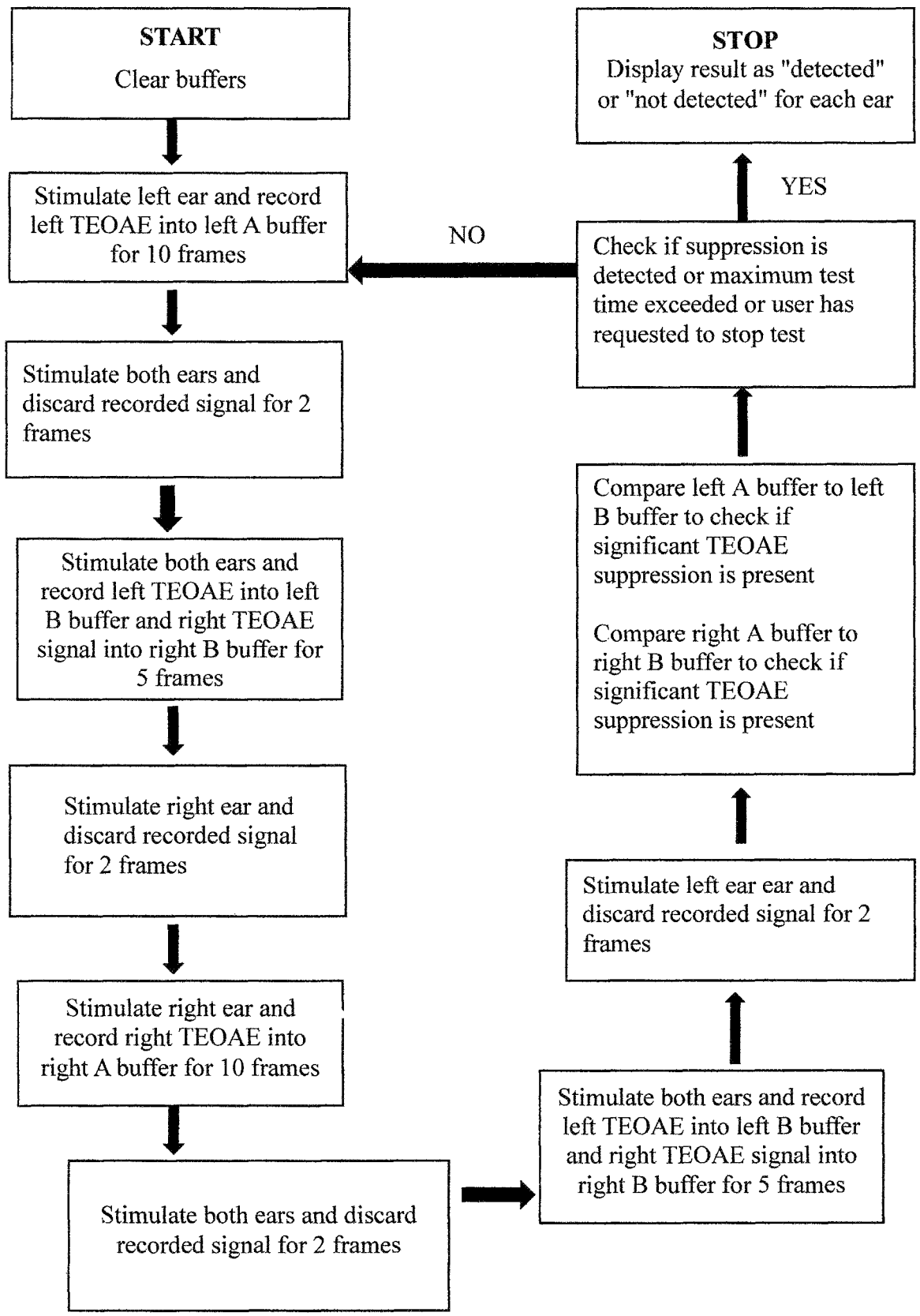
FIG. 3 illustrates a typical flow chart of the TEOAE recording and suppression sequence method described below.

An example of the present testing method is shown in FIG. 3. FIG. 4 illustrates a Table of a periodic sample sequence to record TEOAE CAS suppression of the example of the present method example shown in FIG. 3. The FIG. 4 table reflects 38 frame responses with the results for 10 frames averaged into each of the four buffers. The exact scheme of the present method (10-2-5-2 frames, etc.) may be varied, such as reversing the order, using a different number of frames, etc.

The illustrated repeated steps of the example of FIG. 3 are basically as follows to produce the results shown in the table:

1. Stimulate left ear and record left TEOAE into left A buffer for 10 frames.
2. Stimulate both ears and discard recorded signal for 2 frames.
3. Stimulate both ears and record left TEOAE into left B buffer and right TEOAE signal into right B buffer for 5 frames.
4. Stimulate right ear and discard recorded signal for 2 frames
5. Stimulate right ear and record right TEOAE into right A buffer for 10 frames
6. Stimulate both ears and discard recorded signal for 2 frames.
7. Stimulate both ears and record left TEOAE into left B buffer and right TEOAE signal into right B buffer for 5 frames.
8. Stimulate left ear ear and discard recorded signal for 2 frames.
9. Update graphical representation of test status.
10. Run statistical evaluation of the buffers:
    a. Compare left A buffer to left B buffer to check if significant TEOAE suppression is present.
    b. Compare right A buffer to right B buffer to check if siginificant TEOAE suppression is present.
    c. Check if suppression is detected or maximum test time exceeded or user has requested to stop test, if so, stop, display result as "detected" or "not detected" for each ear; or else repeat from 1

Figure 5:
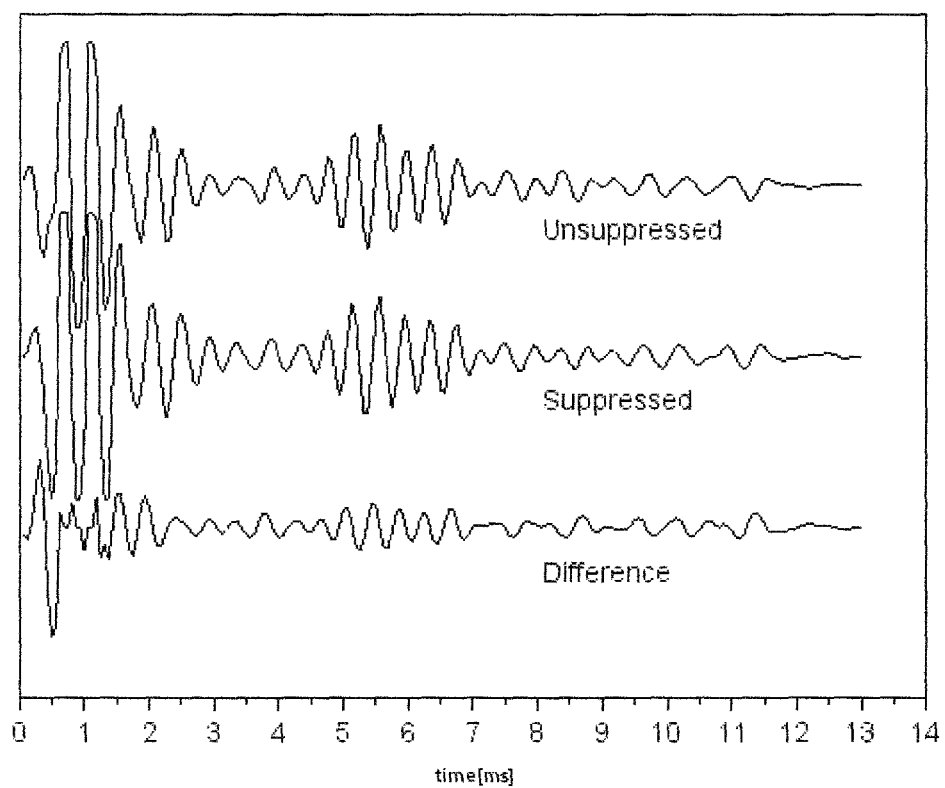
FIG. 5 illustrates sample TEOAE CAS recordings.

FIG. 5 illustrates TEOAE CAS suppressed and unsuppressed recordings, and the net difference.

Figure 6:
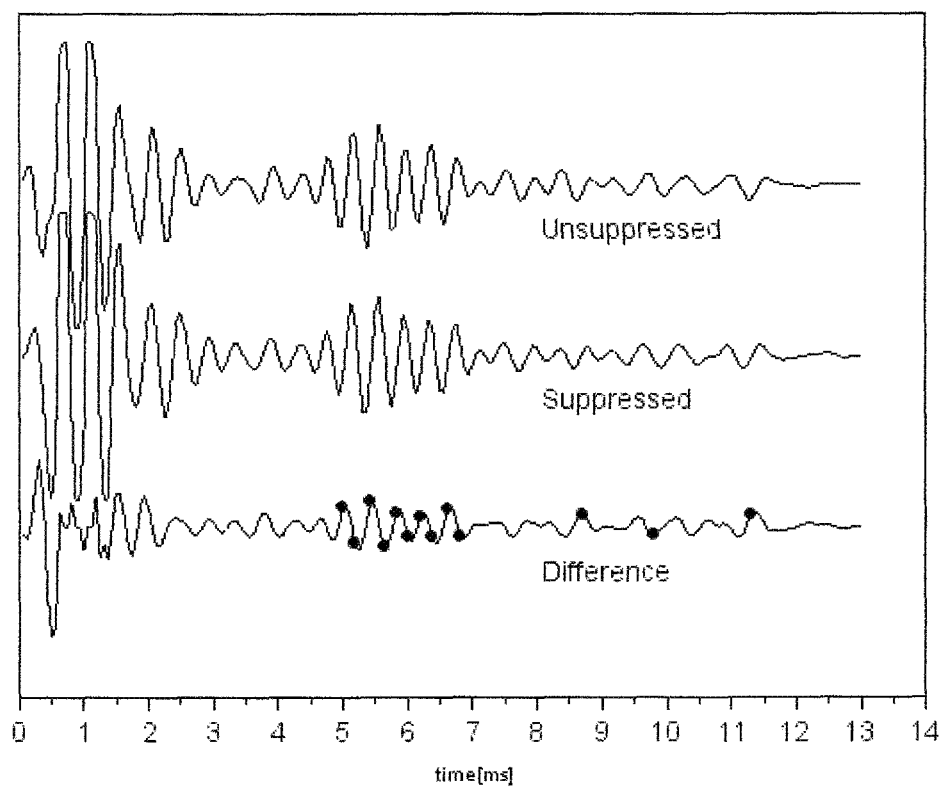
FIG. 6 illustrates a sample TEOAE CAS suppression recording, with significant data points marked in difference traces.

FIG. 6 illustrates a trace if a sample TEOAE CAS recording with significant data points marked in the difference trace.

Figure 7:
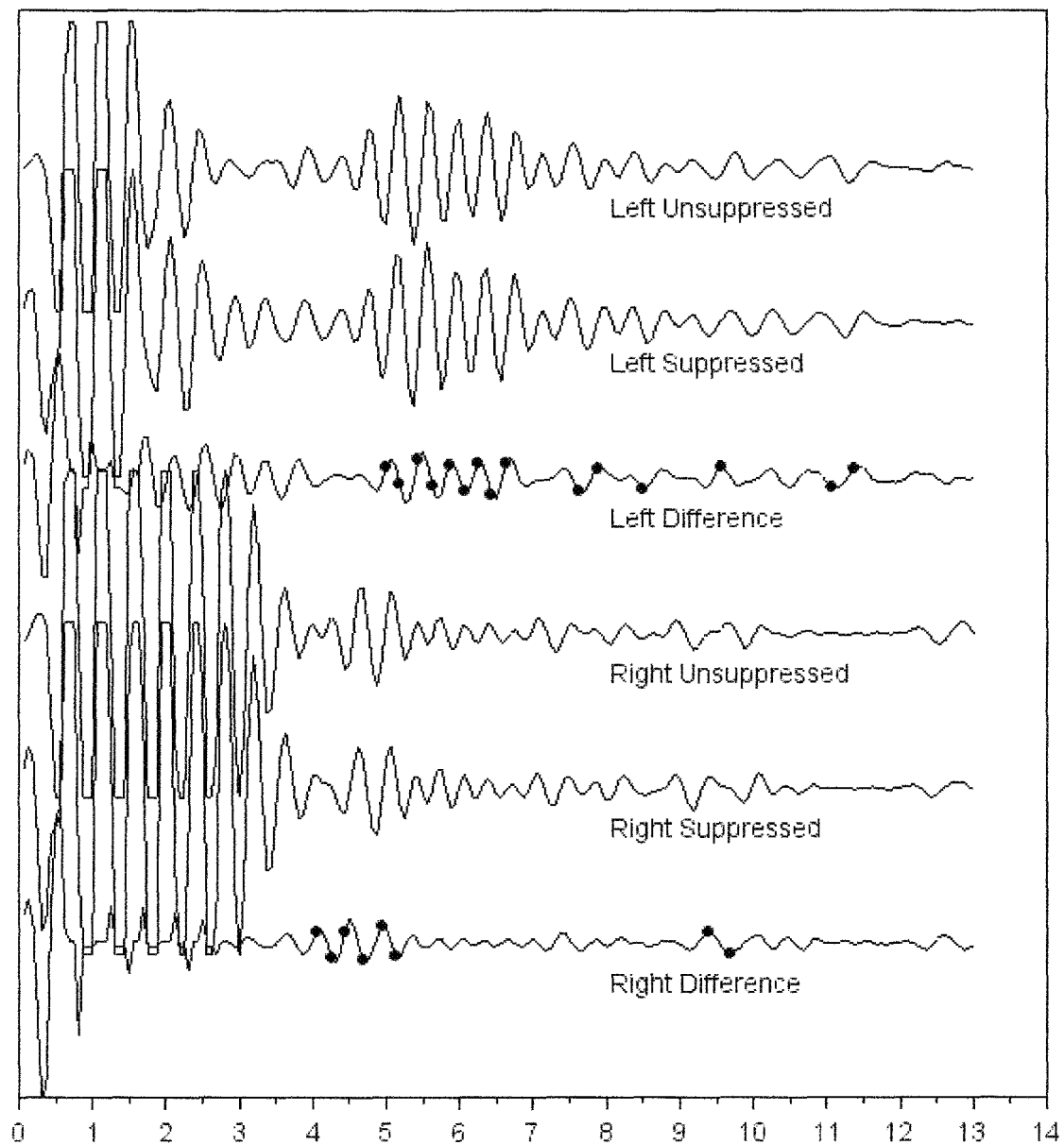
FIG. 7 illustrates a sample TEOAE CAS suppression recording, showing both results from both ears.

FIG. 7 illustrates another sample TEOAE CAS suppression recording, showing responses from both ears, including markers of statistically significant peaks in the different traces. Very high significant suppression is established with 15 peaks for the left ear and 8 peaks for the right ear.

Figure 8:
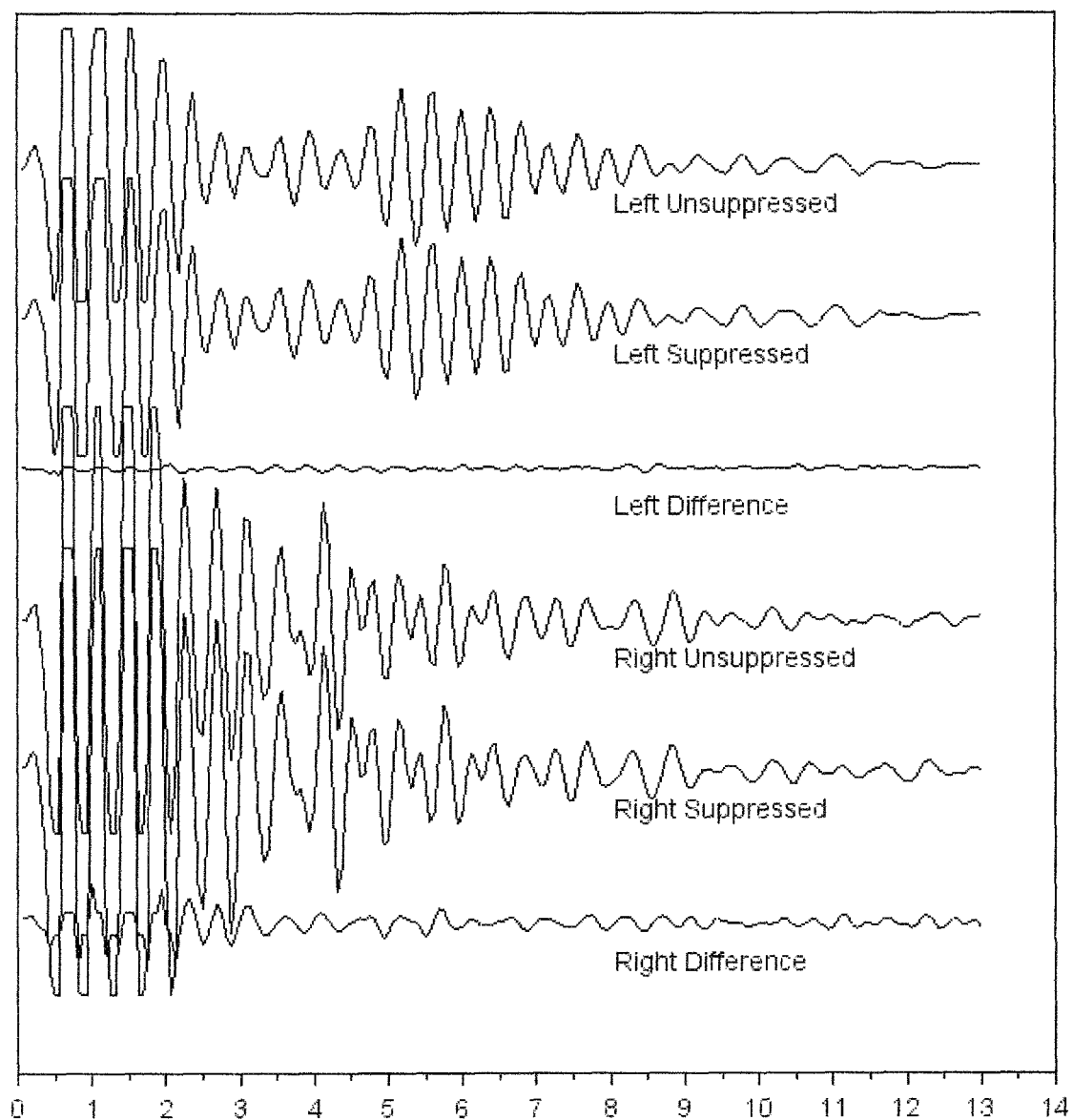
FIG. 8 illustrates a sample TEOAE CAS suppression recording, with absent suppression. The test was recorded in the left ears of two different subjects.

FIG. 8 illustrates a sample TEOAE CAS suppression recording, showing no significant suppression effects. The recording was performed in two ears of two different subjects; therefore no suppression could be expected. No statistically significant peaks were detected.

Figure 9:
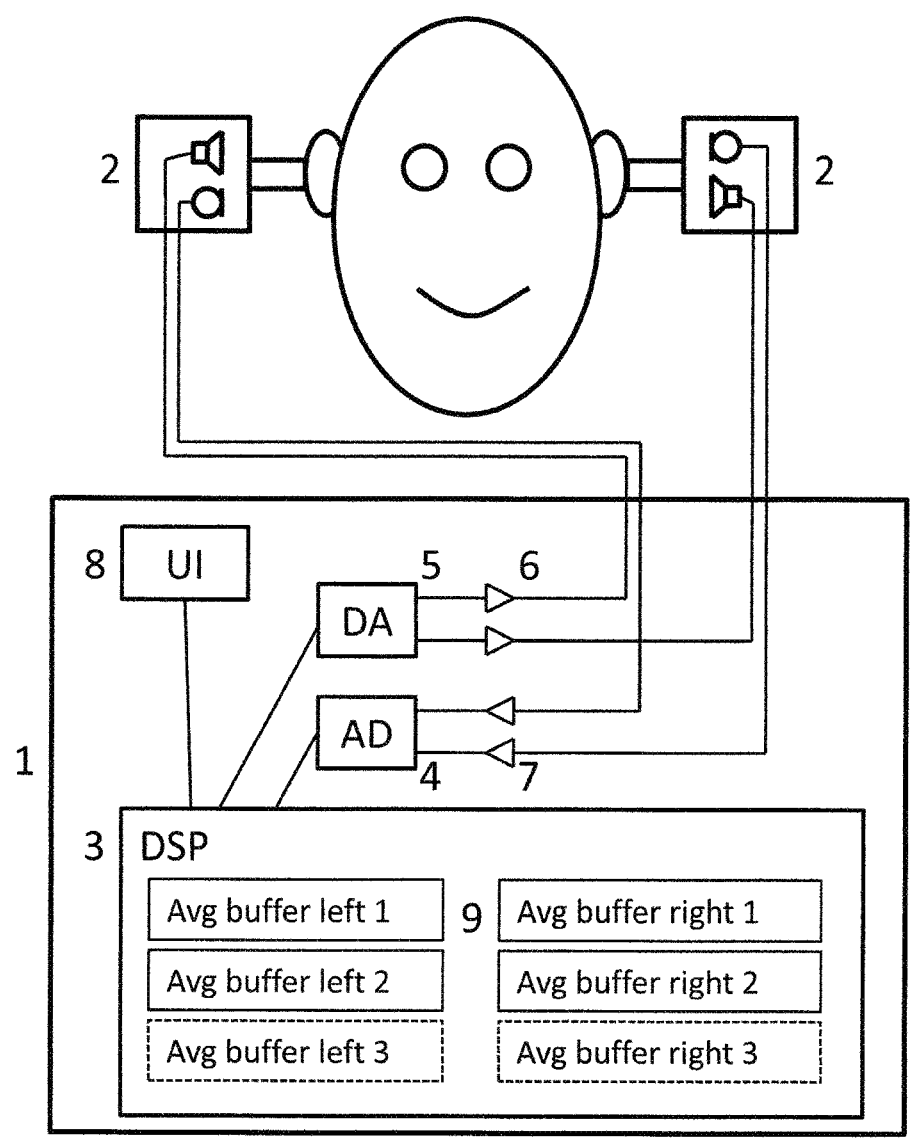
FIG. 9 illustrates an example of a TEOAE CAS suppression recording apparatus.

FIG. 9 illustrates an example of a TEOAE CAS suppression detection and recording apparatus. It comprises:

a) a digital sound processing hardware 1, providing stimulus generation and recording of microphone signals from OAE probes 2. This hardware 1 can consist of a digital signal processor 3, at least two analog-to-digital converters 4, at least two digital-to-analog converters 5, at least two loudspeaker amplifiers 6 and at least two microphone amplifiers 7. It can additionally include means for user interfacing 8, such as display, touch-screens, keyboards, etc. Alternatively, the hardware 1 can provide an interface to a regular computer (not shown), which then provides the user interface and optionally all or parts of the signal processing software.

b) two OAE probes 2, each containing at least one microphone and one loudspeaker, with one placed in each ear of a subject for the test, by means of ear tips(not shown).

c) software (not shown) that implements the methods as described above, either running on the apparatus itself or on a separate computational device, or split at any processing step.

d) means for powering and operating the apparatus and displaying the test results (not shown), by either containing a user interfacing 8 or in communication with a computational device which provides user interfacing.

A possible extension of the method involves using more than two buffers 9 per ear, and recording TEOAE frames after switching on or off into these buffers 9 located in the digital signal processor 3. As a result, one would have TEOAE averaged results for different post-stimulus delays, allowing to inspect the time behavior of TEOAE CAS suppression. The statistical methods as described above can still be used to prove suppression effects. Similar to the known recording of the so-called auditory reflex-decay, the data may be used to diagnose neuronal disorders.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

We claim:

1. A method to automatically detect Transient-evoked Otoacoustic emissions (TEOAE) contralateral suppression, comprising:
   a. exposing a patient to periodic sequences of sound stimuli to generate TEOAE stimuli phase locked waveforms given off by left and right inner ears by periodically switching so as to provide first stimuli to both inner ears, a second stimulus to the left inner ear alone, and a third stimulus to the right inner ear alone;
   b. sequentially recording the TEOAE stimuli phase locked waveforms given off by the left and right inner ears, the left inner ear alone, and the right inner ear alone, wherein:
      i. a left unsuppressed buffer receives and averages all TEOAE stimuli phase locked waveforms that are recorded in the left inner ear at times when the second stimulus is provided to the left inner ear and no stimulus is provided to the right inner ear so as to result in an averaged left unsuppressed TEOAE waveform, ii. a left suppressed buffer receives and averages all TEOAE stimuli phase locked waveforms that are recorded in the left inner ear at times when the first stimuli are provided to the left and right inner ears so as to result in an averaged left suppressed TEOAE waveform, iii. a right unsuppressed buffer receives and averages all TEOAE stimuli phase locked waveforms that are recorded in the right inner ear at times when the third stimulus is provided to the right inner ear and no stimulus is provided to the left inner ear so as to result in an averaged right unsuppressed TEOAE waveform, and iv. a right suppressed buffer receives and averages all TEOAE stimuli phase locked waveforms that are recorded in the right inner ear at times when the first stimuli are provided to the left and right inner ears so as to result in an averaged right suppressed TEOAE waveform;

c. calculating:

i. a difference averaged TEOAE waveform for the left inner ear by subtracting the averaged left suppressed TEOAE waveform from the averaged left unsuppressed TEOAE waveform and ii. a difference averaged TEOAE waveform for the right inner ear by subtracting the averaged right suppressed TEOAE waveform from the averaged right unsuppressed TEOAE waveform; and d. applying morphological analysis to an overall shape of the difference averaged TEOAE waveform for each inner ear to detect if the TEOAE contralateral suppression is present or absent in the right inner ear, the left inner ear, or both right and left inner ears.

2. A method according to claim 1, wherein the exposing of the patient to the periodic sequences of sound stimuli comprises a period with no sound stimulus inserted after each of the first stimuli, the second stimulus, and the third stimulus with no recording of the TEOAE stimuli phase locked waveforms so as to allow recovery from the TEOAE contralateral suppression; or wherein the exposing of the patient to the periodic sequences of sound stimuli comprises a period with a fourth stimulus inserted after each of the first stimuli, the second stimulus, and the third stimulus with no recording of the TEOAE stimuli phase locked waveforms caused by the fourth stimulus so as to allow for settling of suppression effects.

3. A method according to claim 1, wherein the periodic sequences of sound stimuli are user configurable and/or selectable.

4. A method according to claim 1, wherein, when the TEOAE contralateral suppression is detected to be present in one of the left inner ear or the right inner ear, subsequent exposing of the patient to the periodic sequences of the sound stimuli comprises skipping the providing of the respective stimulus to the one of the left inner ear alone or the right inner ear alone and subsequent sequential recording of the TEOAE stimuli phase locked waveforms comprises skipping the respective receiving and averaging all TEOAE stimuli phase locked waveforms that are recorded in the one of the left inner ear alone or the right inner ear alone caused by the respective stimulus so as to speed up the exposing, recording, calculating, and applying so as to determine if the TEOAE contralateral suppression is present or absent in the other of the left inner ear or the right inner ear.

5. A method according to claim 1, wherein applying the morphological analysis to the overall shape of the difference averaged TEOAE waveform for each inner ear comprises counting peaks which exceed a given amplitude above an estimated standard deviation.

6. A method according to claim 1, wherein, when the TEOAE contralateral suppression is detected to be present in one or both of the left inner ear or the right inner ear, the TEOAE contralateral suppression for the one or both of the left inner ear or the right inner ear is represented on a display screen as either "PASS" or "REFER".

7. A method according to claim 1, wherein the method automatically stops when the TEOAE contralateral suppression is detected to be present in one or both inner ears.

8. A method according to claim 1, including adding an extra tone to the step of exposing the patient to periodic sequences of sound stimuli so as to monitor probe stability.

9. An apparatus to automatically detect Transient-evoked Otoacoustic emissions (TEOAE) contralateral suppression comprising:

a. a sound generator configured to expose a patient to periodic sequences of sound stimuli to evoke TEOAE stimuli phase locked waveforms given off by left and right inner ears by periodically switching so as to provide first stimuli to both inner ears, a second stimulus to the left inner ear alone, and a third stimulus to the right inner ear alone;

b. a recorder configured to sequentially record the TEOAE stimuli phase locked waveforms given off by the left and right inner ears, the left inner ear alone, and the right inner ear alone;

c. a left unsuppressed buffer configured to receive and average all TEOAE stimuli phase locked waveforms that are recorded in the left inner ear at times when the second stimulus is provided to the left inner ear and no stimulus is provided to the right inner ear so as to result in an averaged left unsuppressed TEOAE waveform;

d. a left suppressed buffer configured to receive and average all TEOAE stimuli phase locked waveforms that are recorded in the left inner ear at times when the first stimuli is provided to the left and right inner ears so as to result in an averaged left suppressed TEOAE waveform;

e. a right unsuppressed buffer configured to receive and average all TEOAE stimuli phase locked waveforms that are recorded in the right inner ear at times when the third stimulus is provided to the right inner ear and no stimulus is provided to the left inner ear so as to result in an averaged right unsuppressed TEOAE waveform; and f. a right suppressed buffer configured to receive and average all TEOAE stimuli phase locked waveforms that are recorded in the right inner ear at times when the first stimuli is provided to the left and right inner ears so as to result in an averaged right suppressed TEOAE waveform; and g. a computer configured to:

i. calculate a difference averaged TEOAE waveform for the left inner ear by subtracting the averaged left suppressed TEOAE waveform from the averaged left unsuppressed TEOAE waveform, ii. calculate a difference averaged TEOAE waveform for the right inner ear by subtracting the averaged right suppressed TEOAE waveform from the averaged right unsuppressed TEOAE waveform, and iii. apply a morphological analysis to an overall shape of the difference averaged TEOAE waveform for each inner ear to detect if the TEOAE contralateral suppression is present or absent in the right inner ear, the left inner ear, or both right and left inner ears.

10. An apparatus according to claim 9, wherein the sound generator is configured to include a sound stimuli sequence switching so as to provide the first stimuli to both inner ears, the second stimulus to the left inner ear alone, and the third stimulus to the right inner ear alone.

11. An apparatus according to claim 9, wherein the sound generator is configured to provide a period with no sound stimulus inserted after each of the first stimuli, the second stimulus, and the third stimulus and the recorder is configured to not record the TEOAE stimuli phase locked waveforms in these periods with no sound stimulus so as to allow recovery from the TEOAE contralateral suppression, or wherein the sound generator is configured to provide a period with a fourth stimulus inserted after each of the first stimuli, the second stimulus, and the third stimulus and the recorder is configured to not record the TEOAE stimuli phase locked waveforms caused by the fourth stimulus so as to allow for settling of suppression effects.

12. An apparatus according to claim 9, wherein the recorder is user configurable for sequentially recording the TEOAE stimuli phase locked waveforms given off by the left and right inner ears, the left inner ear alone, and the right inner ear alone.

13. An apparatus according to claim 9, wherein, when the TEOAE contralateral suppression is detected to be present in one of the left inner ear or the right inner ear:

the sound generator is configured such that subsequent exposing of the patient to the periodic sequences of the sound stimuli comprises skipping the providing of the respective stimulus to the one of the left inner ear alone or the right inner ear alone, the recorder is configured such that subsequent sequentially recording of the TEOAE stimuli phase locked waveforms comprises skipping recording the TEOAE stimuli phase locked waveforms given off by the one of the left inner ear alone or the right inner ear alone, the left suppressed and unsuppressed buffers and the right suppressed and unsuppressed buffers are configured such that subsequent receiving and averaging skip all TEOAE stimuli phase locked waveforms that are recorded in the one of the left inner ear alone or the right inner ear alone, so as to speed up the detection if the TEOAE contralateral suppression is present or absent in the other of the left inner ear or the right inner ear.

14. An apparatus according to claim 9, wherein the computer is configured to apply the morphological analysis to the overall shape of the difference averaged TEOAE waveform for each inner ear by counting peaks which exceed a given amplitude above an estimated standard deviation.

15. An apparatus according to claim 9, further including a display screen configured to, when the computer detects that the TEOAE contralateral suppression is present or absent in the right inner ear, the left inner ear, or both right and left inner ears, represent the TEOAE contralateral suppression for one or both of the right inner ear and the left inner ear as either "PASS" vs "REFER".

16. An apparatus according to claim 9, wherein the sound generator is configured to automatically stop when the computer detects that the TEOAE contralateral suppression is present or absent in the right inner ear, the left inner ear, or both inner ears.

17. An apparatus according to claim 9, wherein the sound generator includes an extra tone to generate TEOAE feedback to monitor probe stability.

\* \* \* \* \*